United States Patent [19]
Kendall et al.

[11] 4,095,658
[45] Jun. 20, 1978

[54] FLUID MEASUREMENT DEVICE

[75] Inventors: Ray Kendall; Burt Henry McGhee, both of Fort Worth, Tex.

[73] Assignee: Iso AB, Inc., Dallas, Tex.

[21] Appl. No.: 744,121

[22] Filed: Nov. 22, 1976

[51] Int. Cl.² .................. G01G 13/02; G01G 1/18; G01G 1/36; A61M 5/00
[52] U.S. Cl. .................. 177/118; 177/202; 177/250; 177/252; 128/214 E; 128/275
[58] Field of Search .......... 177/60, 112, 118, 245, 177/246, 252, 114, 116, 250, 201, 202; 128/214 E, 275, 276, DIG. 12, DIG. 13

[56] References Cited

U.S. PATENT DOCUMENTS 3,698,494  10/1972  Gaudin .................. 177/245 X

*Primary Examiner*—George H. Miller, Jr.
*Attorney, Agent, or Firm*—Richards, Harris & Medlock

[57] ABSTRACT

A fluid collection, dispensing and measurement device for use in connection with a blood container, for example, and flexible tubing leading thereto. A hollow balance bar, with mobile spherical weights disposed therein is provided and rapid, forceful cut off of the blood flow through the flexible tubing is achieved when the moment created by the filling blood container, accentuated by the motion of the spherical weights, overcomes the moment produced by a preset adjustable counter weight. An adjustable clamping apparatus allows the fluid collection device to be affixed to a stationary object and subsequently adjusted to a level plane to insure accuracy of measurement. A simple modification of the device allows it to be used as a fluid dispensing device. A full container of fluid can be hung on the modified device and a measured quantity of fluid can be dispensed with cut off being achieved as described above.

21 Claims, 10 Drawing Figures

FLUID MEASUREMENT DEVICE

BACKGROUND OF THE INVENTION

In one aspect this invention relates to a fluid measurement and collection device. In another aspect this invention relates to an improved balance bar type blood measurement device which includes the use of a hollow balance bar containing mobile weights which accentuate the rotative cut off action of the balance bar. In still another aspect this invention relates to a blood measurement device which may be easily attached and disattached to either vertical or horizontal bases during use. A further aspect of this invention is that the device may be easily adjusted so that it is positioned in a plane level to the ground thereby facilitating accurate measurement. A still further aspect of the subject invention relates to a fluid dispensing device which can dispense a predetermined quantity of fluid from a fluid container and automatically shut off the fluid supply after the preset quantity of fluid has been dispensed.

Advances in medical technology have made it possible to store blood over extended periods of time for use in surgical operations, or transfusions and the like, as needed. This capability to store blood has made it possible to create blood reserves containing blood collected from donors. Apparatus and procedures for the efficient collection of blood have thus become important in the effort to maintain the flow of blood from donors to those in need. It is generally known that a blood donor should not be allowed to donate more than a specific quantity of blood at one time. The quantity of blood which donors may give at one time varies with the physical conditions of the donor.

In the past, donors were personally attended by medically trained personnel who monitored the donation process. With the advent of "blood banks," however, more efficient donation procedures were desired. One problem was solved by providing an apparatus which would automatically stop the flow of blood from a donor once a specified quantity had been collected. The subject invention relates to an improved type of blood collection measurement device which performs that function.

The most common method of blood collection includes the use of flexible tubing connected with a needle, which is inserted in a blood vessel of a patient's arm for example, and a blood container, such as a plastic bag. Several devices have been made which measure the weight or quantity of the blood collected and at a preselected point stop the flow of blood from the donor to the container by closing off the flexible tubing.

In blood collection, devices which employ a balancing arm to accomplish shut off of the flexible tubing upon rotation of the balancing arm from a level position several operational problems have been encountered. The primary problem is that the unaided rotation of the balance bar, occasioned only by the moment of the blood container at one end of the bar surpassing the moment of a counter weight at the other end of the bar, is relatively slow. This slow rotation is, of course, a result of a slow rate of flow of blood through the flexible tubing into the container. The slow rotation in turn causes the constriction of the flexible tubing to be accomplished slowly resulting in inaccuracies of measurement.

Another problem with balance bar type measurement devices is that they must be carefully leveled with respect to the ground in order for the balancing mechanism to be performed accurately. Accordingly, some of the balance bar type measuring devices now available are provided with their own stand which will insure a level plane for the balance bar so long as the stand itself is placed on a level surface. Inaccuracies may still result, however, if the chosen surface is not level, and in some cases, it may be difficult to find a convenient level surface on which to place the stand. Examples of such prior art devices include those disclosed in U.S. Pat. No. 3,698,494, U.S. Pat. No. 3,557,789, Canadian Pat. No. 581,426, and U.S. Pat. No. 2,784,932.

SUMMARY OF THE INVENTION

According to the subject invention, an improved blood measurement and collection device is provided which provides great accuracy of measurement and which can be easily affixed to either horizontal or vertical bases. Greater accuracy is facilitated by providing a hollow balance bar with mobile weights disposed therein. Upon rotation of the balance bar, when the weight of the blood in the blood collecting bag overcomes the moment produced by an adjustable counter weight, the mobile weights shift rapidly toward the blood collecting bag, thus accentuating the speed of rotation. Thus, forceful cut off of the flexible tubing occurs almost instantaneously and the amount of blood collected can be closely regulated. Furthermore, because of the unique means of attachment, the balance bar can be positioned, with the aid of a bubble vial, in a plane horizontal with the ground. In this manner, optimum efficiency of the balancing mechanism is achieved. Additionally, because of the nature of the clamping means employed, the device can be clamped on a horizontal surface, each as a table, or on a vertical base, such as a support rod.

The device of this invention may also be employed to dispense a measured quantity of fluid. For example, it is sometimes desirable to administer measured quantities of fluids intravenously to a patient. After a simple modification of the device of the subject invention, whereby the position of the balance bar is reversed, a full container of fluid can be hung on one end of the balance bar and rapid and forceful cut off will be achieved once a predetermined amount of fluid has been dispensed.

SHORT DESCRIPTION OF THE DRAWINGS

This invention can be more easily understood from a study of the drawings in which.

DETAILED DESCRIPTION OF THE INVENTION

Figure 1:
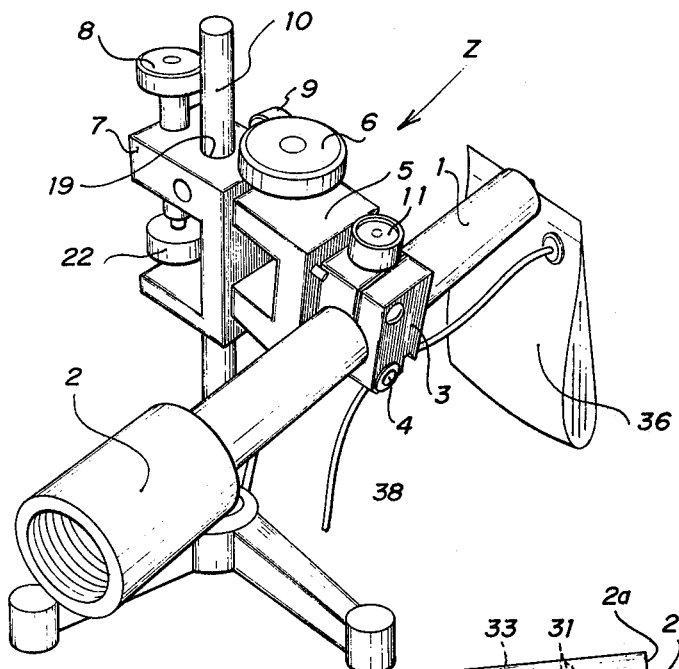
FIG. 1 is a perspective view of the blood measurement device of this invention shown attached to a common type vertical rod stand, and with a blood receptacle attached.

Now referring to the drawings, the blood measurement and collection device Z of this invention will be described in relation to one of its preferred embodiments. Specifically referring to FIG. 1, the major portions of the apparatus are shown. These include a hollow cylindrical balance bar 1 having an adjustable cylindrical counter weight 2 which is threadably engaged with the first end of the balance bar. The balance bar extends through a balance bar mounting member 3 which is pivotally affixed by means of pin 4 to a first rotatably adjustable clamping means 5. The first rotatably adjustable clamping means 5 is shown here in the form of a "C" clamp with locking wheel 6 allowing for adjustment of the position thereof. Adjustable clamping means 5 is clamped on a ball joint (described below) which protrudes from the intermediate face of a second fixed clamping means 7 which is also depicted here as a "C" clamp. Locking wheel 8 allows the second fixed clamping means 7 to be affixed to a horizontal surface (see FIGS. 2-4) and locking wheel 9 allows the second fixed clamping means 7 to be affixed to a vertical rod 10 which can be inserted through apertures in the second fixed clamping means 7 provided therefor. A bubble vial 11 is affixed to the top surface of the balance bar mounting member 3 to aid in the leveling of the device.

Figure 4:
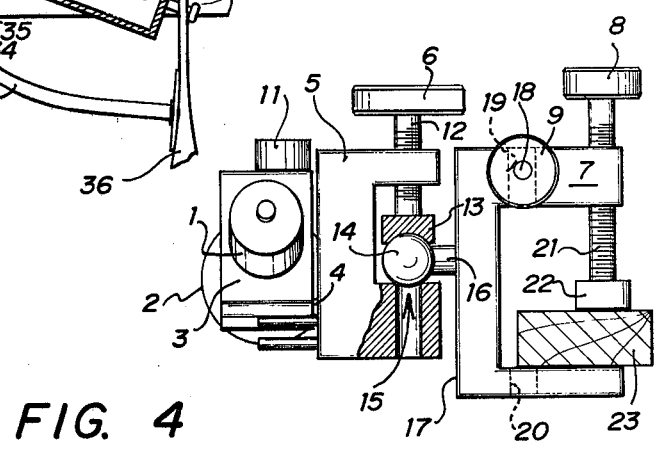
FIG. 4 is an end view of the blood measurement device with a portion of the adjustable clamping means cut away to show the means by which it is attached to the fixed clamping means.

This embodiment of the blood measurement and collection device Z of this invention can be employed to facilitate the accurate collection of a predetermined quantity of blood as follows. The device Z of the subject invention is clamped either to a horizontal surface, a vertical surface or to a rod which is disposed either vertically or horizontally. This versatility regarding the various bases to which the device can be clamped is a result of the dual clamping system employed by the subject invention. Referring to FIG. 4, the first rotatably adjustable clamp 5 is clamped by means of turning locking wheel 6 clockwise which causes threaded clamp shaft 12 to be screwed down until clamping cup 13, affixed to the end of the clamp shaft 12, comes in contact with ball joint 14. A circular depression 15 in the first rotatably adjustable clamp 5, opposite the aperture through which the clamp shaft 12 extends, receives the opposite side of the ball joint 14 so as to firmly clamp it and avoid the possibility of the ball joint 14 slipping out from under the clamping cup 13. Circular depression 15 is depicted in FIG. 4 as a hollow circular shaft extending through the lower portions of the first rotatably adjustable clamp 5.

Ball joint 14 is affixed to ball joint shaft 16 which extends perpendicularly from the intermediate face 17 of the second fixed clamp 7. Locking wheel 9 is affixed to a threaded clamping shaft 18 which upon clockwise rotation of locking wheel 9 moves inward so as to clamp a rod which has been inserted through apertures 19 and 20 (if desired). Locking wheel 8 is affixed to threaded clamping shaft 21 so that when turned clockwise, clamping stopper 22 moves closer to the opposite side of the clamp thereby securely clamping a surface 23 disposed therebetween (as shown).

Figure 2:
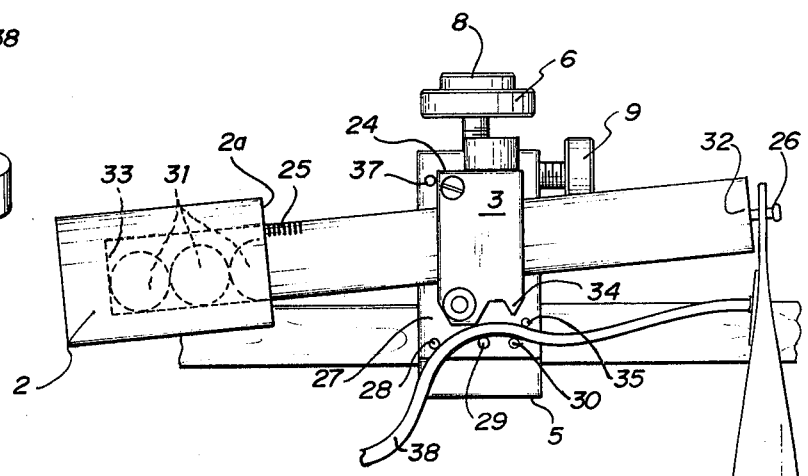
FIG. 2 is a front view of the blood measurement device shown attached to a horizontal surface with flexible tubing and blood receptacle in place, ready to begin receiving blood.
Figure 3:
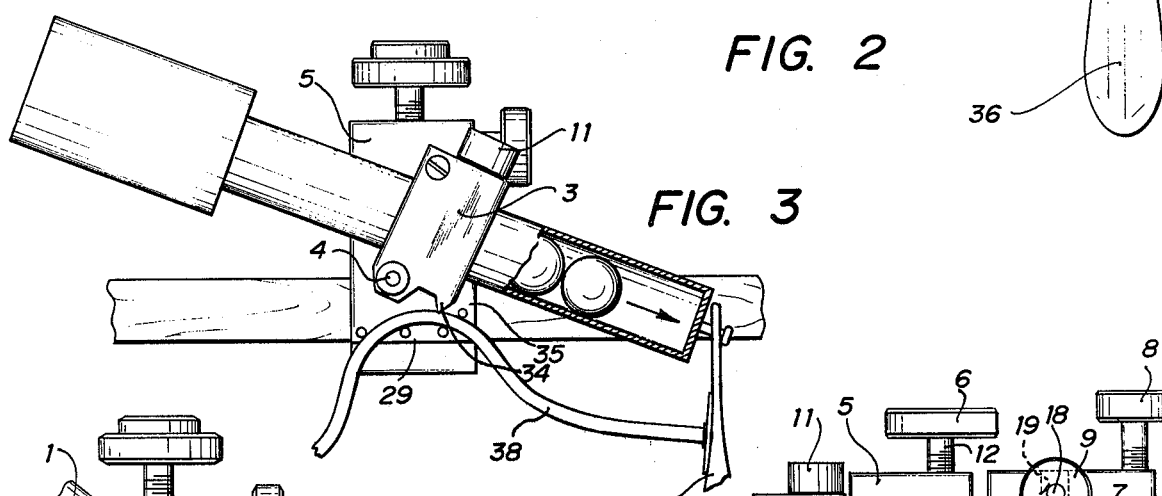
FIG. 3 is also a front view of the blood measurement device with a portion of the hollow balance bar shown cut away to reveal the motion of the mobile weights during rotation of the balance bar.

This dual clamping system provides two independent functions. First, it allows the blood measurement and collection device to be affixed to a variety of surfaces either vertical, horizontal or disposed at an angle. Second, once the device has been affixed to a suitably sturdy surface, the dual clamping means allows adjustment of the position of the balance bar relative to the fixed clamping means and to the ground so that accurate measurements can be performed. Thus, the device can be affixed to a vertical pole by tightening of locking wheel 9 as shown in FIG. 1, or it can be clamped to a horizontal surface, as shown in FIGS. 2-4 by tightening of locking wheel 8. Alternatively, it can be affixed to a horizontal pole or to a vertical surface or to either a pole or surface which is disposed at an angle with respect to the ground.

Once the device has been affixed to a surface, locking wheel 6 can be loosened and the first rotatably adjustable clamp 5 can be rotated around the ball joint 14 until the top surface 24 of the balance bar mounting member 3 lies in a plane parallel with that of the ground. In this manner, accuracy of the gravity dependent weighing process of the subject invention is insured. Bubble vial 11 provides for very accurate adjustment. The bubble vial generally comprises a cylindrical hollow cup with a fluid disposed therein. A bubble of air is allowed to remain in the cup before it is sealed with a transparent material, such as glass or plastic. The transparent material is marked with cross-hatching or a small circle, for example, at its center. Thus, the balance bar mounting member can be leveled by adjusting its position until the bubble in the vial is directly beneath the markings.

Because of the ball joint-clamping cup relationship, the first rotatably adjustable clamp 5 (and the pivotally affixed balance bar 1) can be adjusted by 360° rotation about an axis defined by the longitudinal axis of ball joint shaft 16. In addition, the balance bar 1, mounting member 3 and rotatably adjustable clamp 5 can be rotated about a second axis perpendicular to the longitudinal axis of the ball joint shaft 16. This rotation is limited, however, to the distance between the two clamps (which is determined by the length of the ball joint shaft 16) and by the size of the ball joint 14 with relation to the ball joint shaft 16. For most purposes, only slight rotation about this axis is needed to level the balance bar 1 and mounting member 3, and therefore, the general relationship depicted in FIG. 4 will allow for sufficient adjustment rotation about this second axis. Once the balance bar 1 and mounting member 3 have been leveled with the aid of the bubble vial 11, locking wheel 6 can be turned clockwise to clamp the ball joint 14 firmly, thus holding the desired position.

Once the device has been affixed to a surface or rod and adjusted to a level position, the adjustable counter weight 2, which is threadably engaged with the first end of the balance bar 1, is adjusted until the edge 2a of the counter weight 2 closest to the middle of the balance bar 1 is aligned with a hatch mark 25 designating a quantity or weight of blood to be collected. Various hatch marks 25 can be etched or painted on the side of the balance bar so that a broad range of settings is possible. The position of the hatch marks 25 may be determined so as to take into account the average weight of the blood container to be employed in connection with this device.

The blood container 36, such as a plastic bag, for example, is then hung from a shaft 26 protruding perpendicularly from the face of end 32 of the balance bar 1. The shaft may be knobbed at the end as depicted in FIGS. 2-4 so as to prevent the blood container from becoming detached once rotation of the balance bar has occurred. In addition, any other means of attaching the blood container to the end of the balance bar can be employed such as snaps or hooks, for example. The flexible tubing 38 used as a conduit for blood flowing from the donor to the blood container 36 is then positioned on the front face 27 of the first rotatably adjustable clamp 5 by lacing it through pegs 28, 29 and 30 in the following manner. The tubing 38 can be threaded between pegs 28 and 29 and over the top of pegs 29 and 30, as shown in FIGS. 2 and 3. Peg 35 can be affixed to the front face 27 of the first rotatably adjustable clamp 5 such that it angles downward at an angle of about 30. When this is done, the flexible tubing 38 can be snapped between pegs 35 and 30 and it will be firmly held in place.

Once the tubing 38 has been positioned, the donation of blood by the donor can begin. Because the flexible tubing 38 is not constricted in any way until rotation of the balance bar 1, blood will flow freely into the blood container 36. However, at the instant at which the moment created by a quantity of blood collected in the blood container 36 exceeds the moment created by the preset counter weight 2, the balance bar 1 will begin to rotate in a clockwise direction. Conventional blood collection and measurement devices employing this type of rotation to obtain cut off of the blood flow suffer from a serious disadvantage. Since the flow of blood into the blood container is at a relatively slow rate, the rotative action of the balance bar will also be slow and will usually lack sufficient force to obtain cut off instantaneously. In the subject invention, a mobile weight means is disposed within the balance bar. FIG. 2 depicts this weight means as spheres, e.g., common metal balls 31. In addition, single weights could be used or liquid mercury could be employed.

Referring to FIGS. 2 and 3, the rotative action and resulting cut off of the flow of blood to the blood container 36 will be described. FIG. 2 shows metal balls 31 at rest prior to any rotation. The metal balls 31 will remain in this position until the exact instant at which the weight of the blood collected in the blood container 36 overcomes the moment of preset adjustable counter weight 2. At this instant, the second end 32 of the balance bar 1, from which the blood container 36 is suspended, begins to rotate downward causing the first end 33 of the balance bar 1, in which the metal balls 31 are disposed, to move upward. At the exact instant at which the second end 32 reaches a lower position than the first end 33, the metal balls 31 rapidly travel from their rest position toward the second end 32. FIG. 3 depicts the path of the metal balls 31 at a point just prior in time to the achievement of cut off of the flow of blood through the flexible tubing 38.

Upon rotation, as shown in FIG. 3, triangular extension 34 which protrudes from balance bar mounting member 3 travels in an arc which intersects pegs 29 and 30. Thus, upon full rotation, triangular extension 34 nips the flexible tubing 38 by squeezing it between pegs 29 and 30.

It should be noted that the cut off action occurs rapidly and forcefully as a result of the accentuated rotative movement of the balance bar 1 induced as a result of the force imparted by the rolling metal balls 31. Peg 35 is positioned on the front face 27 of the first rotatably adjustable clamp 5 in a manner such that it stops rotation of the balance bar mounting member 3 about its axis defined by pin 4. Furthermore, peg 35 is positioned such that triangular extension 34 will be stopped in its arced path at a point just prior to contact with the peg 29. In this manner, the flexible tubing 38 disposed therebetween can be cut off by collapsing its walls without the danger of severing the flexible tubing 38 completely, which would result in a loss of blood.

Having collected a predetermined quantity of blood and achieved rapid and accurate cut off, the blood container 36 and flexible tubing 38 can then be easily removed from the subject invention for further processing. An important feature of this invention is that upon removal of the blood container 36, it automatically resets itself and, unless a different quantity of blood is desired to be collected, may be reused without any re-adjustments. This automatic resetting action is facilitated by disposing the balance bar 1 at a slight angle with respect to the balance bar mounting member 3. The balance bar 1 is inclined so that the first end 33 is lower than the second end 32 when the balance bar 1 is at rest. Peg 37 prevents rotation of the balance bar mounting member 3 (and thereby the balance bar 1 itself) past this rest position. Thus, upon removal of the blood container 36 from shaft 26 on the second end 32 of the balance bar 1, the moment of the counter weight 2 will cause the balance bar to rotate back to its rest position. In addition, because the first end of the balance bar 1 is lower than the second end 32 at the rest position, the metal balls 31 will travel through the hollow balance bar 1 and come to rest against the first end 33 of the balance bar 1. The device is then ready for a second use, and if the same quantity of blood is desired to be collected, all that need be done is to attach the blood container 36 and properly position the flexible tubing 38.

Figure 5:
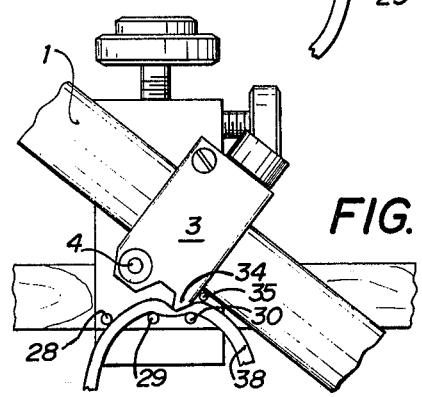
FIG. 5 is a fragmented front view of that portion of the blood measurement device which pinches closed the flexible tubing, shown in an actuated position.

FIG. 5 depicts the manner in which triangular extension 34 squeezes flexible tubing 38 completely closed upon full rotation of balance bar 1. Peg 35 arrests the rotation of balance bar 1 and its mounting member 3, about the axis defined by pin 4, at a point such that a gap is left between triangular extension 34 and peg 29 which is approximately the same as the thickness of a section of completely collapsed flexible tube 38. This arrangement provides for complete shut off of the flexible tubing 38 without the danger that triangular extension 34 may sever the tubing against peg 29. Actual cut off is achieved by the squeezing action of triangular extension 34 as it passes between pegs 29 and 30.

Figure 6:
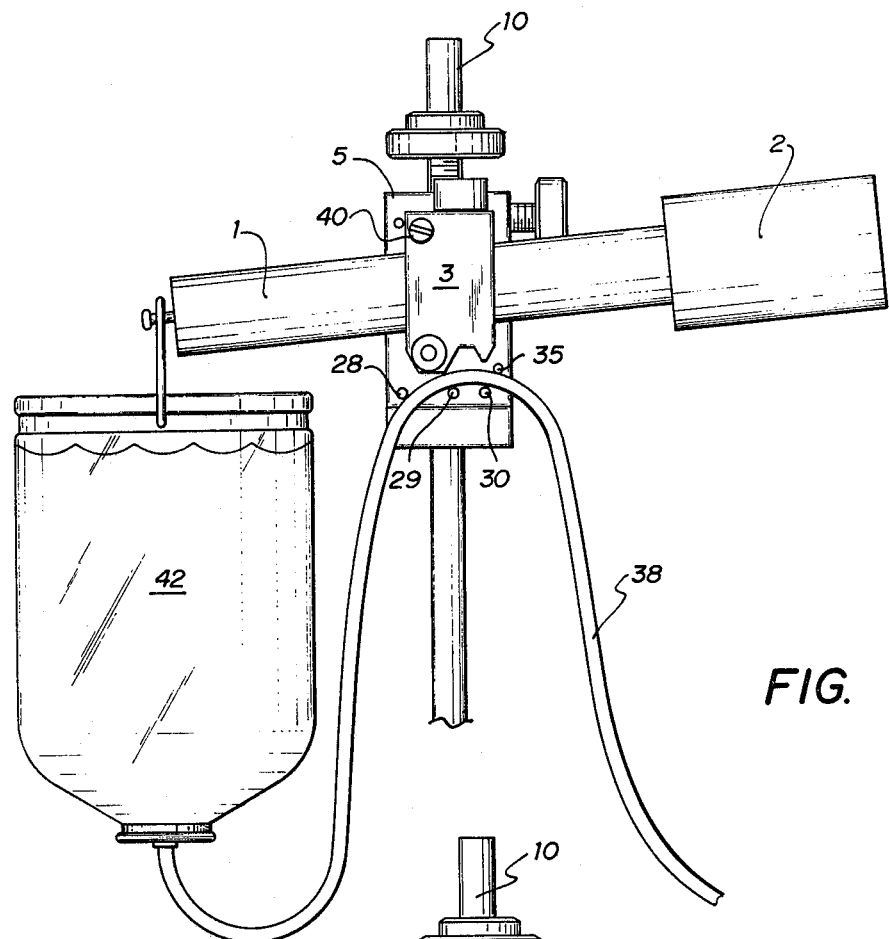
FIG. 6 is a front view of the device of the present invention shown modified for use as a fluid dispensing device with a full fluid container attached.

FIG. 6 depicts the device of the present invention after it has been modified for use as a fluid dispenser. The necessary modification can be accomplished by loosening screw 40 on the front face of the balance bar mount 3 and removing the balance bar 1 from its mount. The balance bar 1 is then reinserted through balance bar mount 3 in the reverse position such that the counter weight 2 is on the right hand side of the balance bar mount when viewed from the front, as shown in FIG. 6. A dispensing bottle 42 or other fluid container which contains the fluid to be dispensed is hung on shaft 26. The counter weight 2 is on the right hand side of the balance bar mount when viewed from the front, as shown in FIG. 6. A dispensing bottle 42 or other fluid container which contains the fluid to be dispensed is hung on shaft 26. The counter weight 2 can be set to the desired hatch mark 25 setting corresponding to the amount of fluid to be dispensed.

Figure 7:
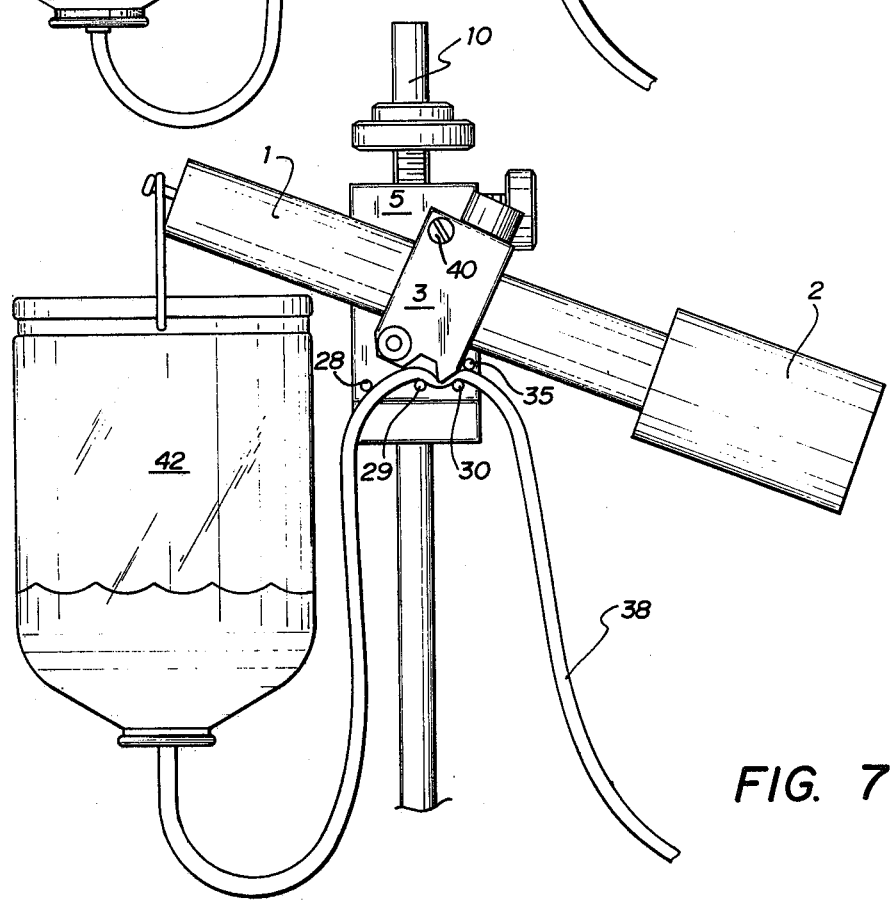
FIG. 7 is the same as FIG. 6 but shows the cut off action which occurs once a predetermined amount of fluid has been dispensed from the fluid container.

FIG. 7 depicts the modified device of the present invention, as shown in FIG. 6, after the desired quantity of fluids has been dispensed. Once the fluid content of dispensing bottle 42 is reduced by the desired, preset amount, the balance bar will rotate rapidly clockwise and will cut off the flow of fluid through flexible tubing 38 in the same manner as described above.

Figure 8:
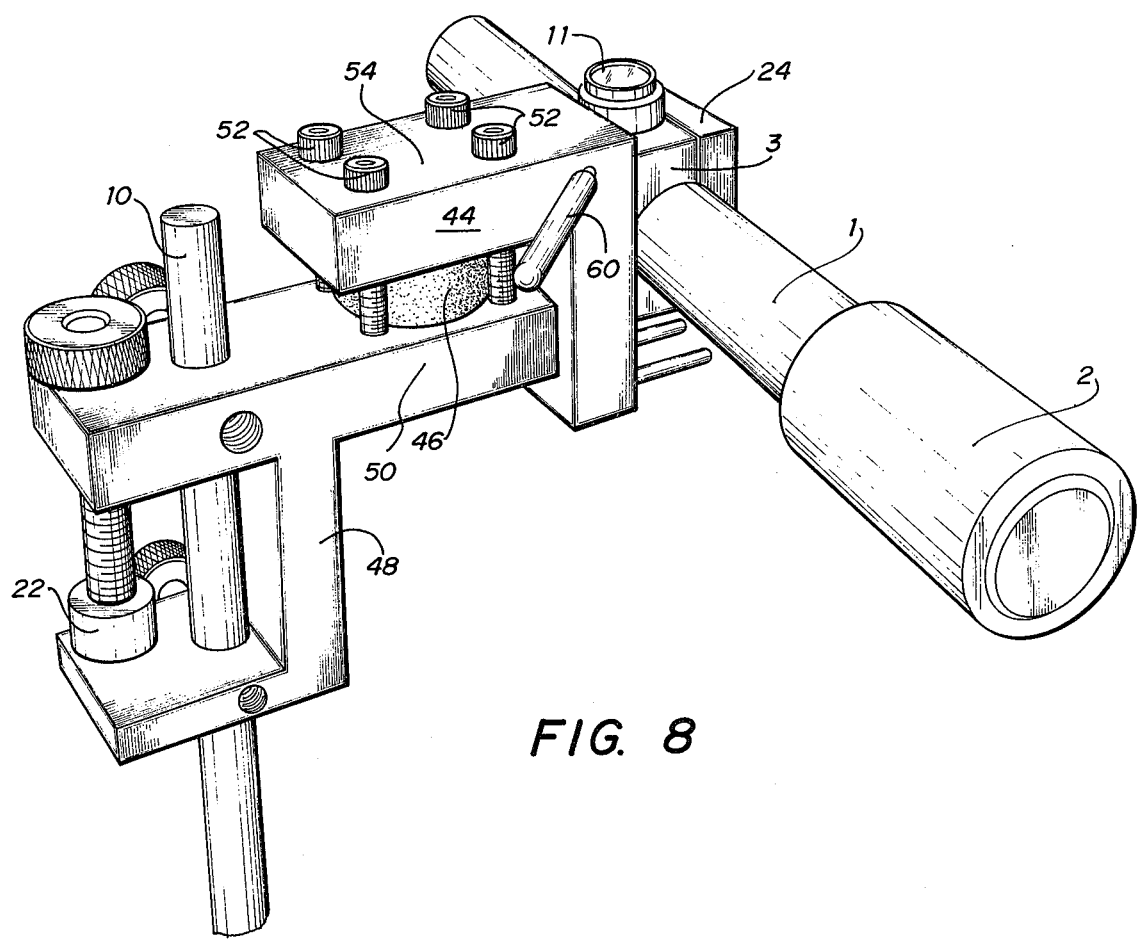
FIG. 8 is a perspective view of a second embodiment of the blood measurement device of this invention shown attached to a common type vertical rod stand.

FIG. 8 depicts a second embodiment of the blood measurement device of the present invention. This embodiment operates in all respects exactly like the embodiment depicted and described in FIGS. 1-7 except that the means for leveling the balancing mechanism by adjusting the top surface 24 of balance bar mounting member 3 so that it lies in a plane parallel with the ground differs in the respects described below. In place of the dual C-clamp arrangement (as shown in detail in FIG. 4) which includes rotatably adjustable C clamping means 5 which clamps onto ball joint 14, the embodiment depicted in FIG. 8 provides an L-shaped adjustable clamping means 44 (to which the balance bar mounting member 3 is pivotably attached), an elastically deformable cushioning member 46, and a modified fixed clamping means 48, which in place of ball joint 14 and its shaft 16 provides an extension arm 50 on which is disposed the elastically deformable cushioning member 46 (shown in FIG. 8 in the form of a cylinder).

Figure 9:
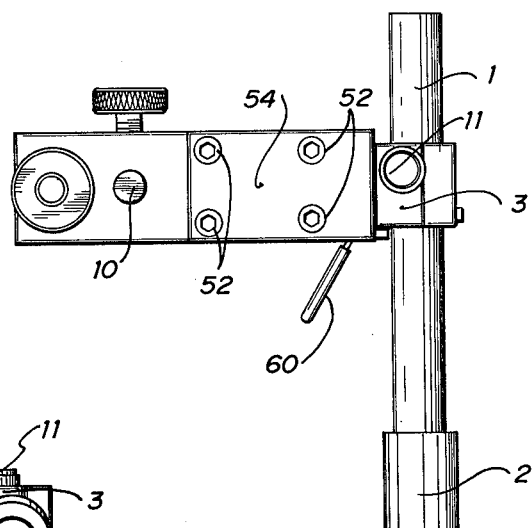
FIG. 9 is a top view of the embodiment of the present invention shown in FIG. 8.

As shown in FIG. 9, a plurality of threaded leveling means 52 are positioned in a plurality of apertures which extend through the top surface 54 of adjustable clamping means 44. The apertures are located along the outside circumference of elastically deformable cushioning member 46 such that the leveling means 52 pass through the top surface 54 of fixed clamping means 44 and are received in threaded apertures provided in extension arm 50 of fixed clamping means 48. Thus, leveling means 52 (shown in the form of threaded screws) extend through top surface 54 of adjustable clamping means 44, along the periphery of the circumference of elastically deformable cushioning means 46, and into threaded apertures provided in extension arm 50. As is clear from a study of FIG. 10, the elastically deformable cushioning means 46 is disposed between adjustable clamping means 44 and fixed clamping means 48 and is held in place by compression applied to these two clamping means by leveling means 52. Because cushioning means 46 is elastically deformable, tightening or loosening of the leveling means 52 disposed around the circumference thereof, will cause the cushioning member to compress or expand to its normal shape according to the compression applied at various points around its periphery by leveling means 52. By tightening or loosening selected leveling means in this manner, adjustable clamping means 44 may be adjusted to a horizontal position with respect to the ground. Accuracy of such adjustment is insured by use of bubble vial 11 previously described. In the preferred form of this embodiment of the invention, the elastically deformable cushioning means is cylindrical in shape and can, for example, be a puck-like piece of neoprene rubber. While any plurality of leveling means 52 can be used, the preferred number is three disposed substantially equidistant around the periphery of the circumference of the elastically deformable cylinder.

Figure 10:
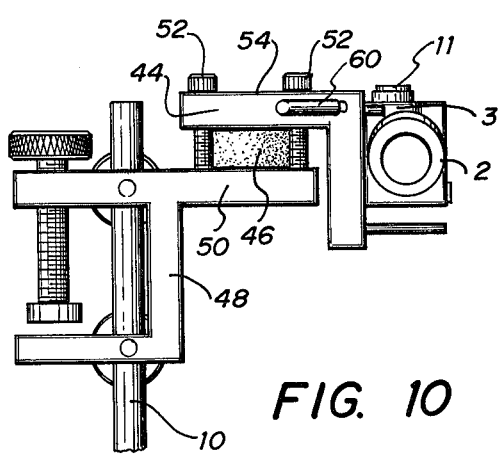
FIG. 10 is a side view of the embodiment of the present invention shown in FIGS. 8 and 9.

Additionally, FIGS. 8-10 depict a shaft 60 affixed to L-shaped adjustable clamping means 44 at an angle away from the balance bar 1. This shaft 60, or its equal, is used to hold flexible tubing away from the balance bar so that extra flexible tubing will not rest on balance bar 1 during operation thereby causing inaccuracies in measurement. As shown here, shaft 60 includes a sheath of rubbery material to provide for good frictional holding properties between the shaft and the flexible tubing. Use of a shaft 60 or the like in conjunction with the embodiment of the present invention set forth in FIGS. 1-7 can be accomplished by affixing a shaft 60 to rotatably adjustable clamping means 5.

As is apparent from a comparison of the embodiment of the present invention shown in FIGS. 1-7 to the embodiment described above and shown in FIGS. 8-10, operation of both embodiments of the invention is substantially the same whether the device is used as a fluid dispensing or collecting means. The embodiment described and shown in FIGS. 8-10 merely provides for an alternative method for leveling the device so that accuracy of the balancing mechanism is insured.

While this invention has been described in relation to its preferred embodiment, it is to be understood that various modifications thereof will now be apparent to one skilled in the art upon reading the specification and it is intended to cover such modifications as fall within the scope of the appended claims.

We claim:

1. A fluid collection and dispensing device for use in connection with a fluid container and flexible tubing leading thereto comprising:
    (a) a hollow balance bar having a first closed end and a second closed end;
    (b) a balance bar mounting member through which said balance bar extends, pivotally attached to a first rotatably adjustable clamping means;
    (c) a second fixed clamping means comprising a means for rotatable attachment of said first adjustable clamping means;
    (d) spherical weights disposed within said hollow balance bar;
    (e) an adjustable counter weight, operatively engaged with said first end of said balance bar;
    (f) opposing flexible tube constricting means on said balance bar mounting member and said first rotatably adjustable clamping means; and
    (g) a means for attaching a hanging fluid container affixed to said second end of the balance bar.

2. The apparatus of claim 1 wherein said opposing flexible tube constricting means comprise peg means affixed perpendicularly to said first rotatably adjustable clamping means below the pivotal axis of said balance bar, for holding the flexible tubing, and a pinch off member projecting from said balance bar mounting member which upon rotation of said balance bar intersects the point at which the flexible tubing is held by said peg means to thereby constrict said flexible tubing therebetween.

3. The apparatus of claim 2 and further comprising a bubble vial level means affixed to the upper surface of said balance bar mounting member.

4. The apparatus of claim 3 wherein said first rotatably adjustable clamping means comprises a "C" shaped clamp means.

5. The apparatus of claim 4 wherein said second fixed clamping means comprises a "C" shaped clamp means.

6. The apparatus of claim 5 wherein the means for rotatable attachment of said first rotatably adjustable clamping means to said second fixed clamping means comprises a ball joint means affixed to said second fixed clamping means and intermediate of said first rotatably adjustable clamping means and said second fixed clamping means.

7. The apparatus of claim 6 wherein said balance bar is cylindrical.

8. The apparatus of claim 7 wherein said adjustable counter weight is cylindrical and threadably engaged with said first end of said balance bar.

9. In a blood collection and measurement device which comprises a balance bar having a first end and a second end, a pivotal mounting means adjacent its midsection, and with a means for attaching a blood collection container to said first end and a counterweight means operatively attached to said second end and having opposed flexible tube constricting means positioned on said balance bar and on a mount to which said balance bar is pivotally connected, the improvement comprising a hollow channel contained within said balance bar along the length thereof and containing mobile weight means which travel within said channel along a path traversing said pivotal mounting means to thereby accentuate the rotation speed of said balance bar as said first end and second end rotate about said pivotal mount.

10. The improved blood collection and measurement device of claim 9 further comprising a rotatably adjustable attachment means for attaching said device to a stationary object comprising a first rotatably adjustable mounting means to which such balance bar is pivotally attached and a second fixed clamping means for attachment to a stationary object, said second fixed clamping means comprising a means for rotatable attachment for said first rotatably adjustable mounting means.

11. The improved blood collection and measurement device of claim 10 further comprising a bubble vial level means affixed adjacent said pivotal mounting means on said balance bar.

12. A device for the collection and measurement of blood for use in conjunction with a blood container and flexible tubing leading thereto and providing for automatic shut off at a predetermined quantity of collected blood comprising a cylindrical hollow balance bar, having a first closed end and a second closed end, said balance bar extending through a balance bar mounting member which is pivotally attached to an assembly comprising a first rotatably adjustable clamping means, and a second fixed clamping means comprising a means for rotatable attachment for said first rotatably adjustable clamping means, and further comprising a cylindrical adjustable counter weight threadably attached to the first end of said balance bar, spherical weights disposed within said hollow balance bar, a means for attaching a hanging blood container affixed to said second end of the balance bar, opposing constricting means comprising two pegs for holding flexible tubing in place affixed perpendicularly to the balance bar pivoting face of said first rotatably adjustable clamping means and a triangular extension of said balance bar mounting means which upon rotation of said balance bar intersects the point at which the flexible tubing is held by said pegs, and a bubble vial level means affixed to said balance bar mounting means.

13. In a fluid dispensing and measurement device which comprises a balance bar having a first end and a second end, a pivotal mounting means adjacent its midsection, and with a means for attaching a fluid dispensing container to said first end and a counterweight means operatively attached to said second end, the improvement comprising a hollow channel contained within said balance bar along the length thereof and containing mobile weight means which travel within said channel along a path traversing said pivotal mounting means to thereby accentuate the rotation speed of said balance bar as said first end and second end rotate about said pivotal mount.

14. A fluid collection and dispensing device for use in connection with a fluid container and flexible tubing leading thereto comprising:
(a) a hollow balance bar having a first closed end and a second closed end;
(b) mobile weights disposed within said hollow balance bar;
(c) a balance bar mounting member through which said balance bar extends, pivotally attached to an adjustable clamping means;
(d) a fixed clamping means;
(e) an elastically deformable cushioning member disposed intermediate of said adjustable clamping means and said fixed clamping means;
(f) a plurality of threaded leveling means disposed around the periphery of said cushioning member, through said adjustable clamping means and threadably received in said fixed clamping means;
(g) an adjustable counter weight, operatively engaged with said first end of said balance bar;
(h) opposing flexible tube constricting means on said balance bar mounting member and said first adjustable clamping means; and
(i) a means for attaching a hanging fluid container affixed to said second end of the balance bar.

15. The device of claim 14 wherein the number of said threaded leveling means is three.

16. The apparatus of claim 14 wherein said opposing flexible tube constricting means comprise peg means affixed perpendicularly to said first adjustable clamping means below the pivotal axis of said balance bar, for holding the flexible tubing, and a pinch off member projecting from said balance bar mounting member which upon rotation of said balance bar intersects the point at which the flexible tubing is held by said peg means to thereby constrict said flexible tubing therebetween.

17. The apparatus of claim 16 and further comprising a bubble vial level means affixed to the upper surface of said balance bar mounting member.

18. The apparatus of claim 17 wherein said balance bar is cylindrical.

19. The apparatus of claim 18 wherein said adjustable counter weight is cylindrical and threadably engaged with said first end of said balance bar.

20. The device of claim 19 wherein said cushioning member is cylindrical.

21. The device of claim 20 wherein said cushioning member is composed of neoprene.

* * * * *